United States Patent
Richter et al.

(10) Patent No.: US 10,064,711 B1
(45) Date of Patent: Sep. 4, 2018

(54) SMART TOOTHBRUSH AND FLOSS METHOD AND SYSTEM

(71) Applicant: Click Care LLC, Saginaw Charter Township, MI (US)

(72) Inventors: William Richter, Saginaw, MI (US); Nevin Steinbrink, Saginaw, MI (US)

(73) Assignee: Click Care LLC, Saginaw Charter Township, MI (US)

( * ) Notice: Subject to any disclaimer, the term of this patent is extended or adjusted under 35 U.S.C. 154(b) by 0 days.

(21) Appl. No.: 15/667,571

(22) Filed: Aug. 2, 2017

Related U.S. Application Data

(63) Continuation-in-part of application No. 14/494,534, filed on Sep. 23, 2014, now abandoned.

(60) Provisional application No. 61/881,425, filed on Sep. 23, 2013.

(51) Int. Cl.
| | |
|---|---|
| *A61C 15/04* | (2006.01) |
| *A61C 17/34* | (2006.01) |
| *A46B 15/00* | (2006.01) |
| *A61C 17/22* | (2006.01) |
| *A61C 17/32* | (2006.01) |
| *A41H 1/02* | (2006.01) |
| *G06K 9/00* | (2006.01) |

(52) U.S. Cl.
CPC ............ *A61C 17/221* (2013.01); *A41H 1/02* (2013.01); *A46B 15/0004* (2013.01); *A46B 15/0012* (2013.01); *A46B 15/0014* (2013.01); *A61C 15/047* (2013.01); *A61C 17/22* (2013.01); *A61C 17/225* (2013.01); *A61C 17/32* (2013.01); *A61C 17/34* (2013.01); *G06K 9/00201* (2013.01)

(58) Field of Classification Search
CPC .............................. A61C 17/221; A61C 17/34
See application file for complete search history.

(56) References Cited

U.S. PATENT DOCUMENTS

| | | | | |
|---|---|---|---|---|
| 2012/0295216 | A1* | 11/2012 | Dykes ................ | A61C 17/22 433/27 |
| 2013/0091642 | A1* | 4/2013 | Dykes ................ | A46B 15/0008 15/22.1 |

* cited by examiner

*Primary Examiner* — Randall Chin
(74) *Attorney, Agent, or Firm* — Staniford Tomita LLP

(57) ABSTRACT

A toothbrush system includes a toothbrush having a floss pick with position sensors. The position sensors can be used to create a digital representation of the user's mouth and by monitoring the movement of the toothbrush while in use, the system can determine if all surface areas of the teeth have been properly brushed based upon the measured brush time and force. The system can determine if the teeth have been properly flossed based upon the measured floss time and position. If any areas of the teeth have not been properly brushed or flossed, the system can emit a signal informing the user of the areas that need additional brushing or flossing.

20 Claims, 9 Drawing Sheets

SMART TOOTHBRUSH AND FLOSS METHOD AND SYSTEM

CROSS REFERENCE TO RELATED APPLICATIONS

This application is a continuation in part of U.S. patent application Ser. No. 14/494,534 "Smart Toothbrush Method And System" filed on Sep. 23, 2014, now abandoned, which claims priority to U.S. Provisional Patent Application No. 61/881,425. "Method And System Of A Smart Toothbrush" filed Sep. 23, 2013, the contents of which are hereby incorporated by reference in its entirety.

BACKGROUND

The toothbrush is an instrument used to clean the teeth and gums that consists of a head of tightly clustered bristles mounted on a handle, which facilitates the cleansing of hard-to-reach areas of the mouth. An electric toothbrush performs oscillations or rotations of its bristles, driven by a motor. Electric brushes can be classified into two categories according to the type of action that they employ: vibration or rotation-oscillation. When using vibrating toothbrush, a brushing technique similar to that used with a manual toothbrush is recommended, whereas with rotating-oscillating brushes the recommend cleaning technique is to simply move the brush slowly from tooth to tooth.

SUMMARY OF THE INVENTION

The present invention is directed towards a smart toothbrush and floss system having a plurality of sensors coupled to a processor for detecting the position, force and movement of the toothbrush. The system can include a memory for storing a digital representation of the outer surfaces of the user's teeth and the junctions of adjacent teeth. In an embodiment, the digital representation of the outer surfaces of the user's teeth can be in the form of a point cloud. The user information can include missing and/or false teeth. The system can also store a predetermined amount of time that each surface of the teeth should be brushed at a predetermined force or pressure that should be applied by the user.

The system can compare the force and time that that the user has moved the bristles of a toothbrush against the outer surfaces of the teeth. Based upon the force, movement and time measurements, the system can determine if all surface areas of the teeth have been properly cleaned. If an area(s) of the teeth has not been properly cleaned based upon an improper force, the system can transmit a signal to an output device to inform the user increase or decrease the force applied to the toothbrush. If the user does not spend the required time or misses brushing an area of the teeth, the system can emit an output signal informing the user of the area(s) that needs additional brushing.

In addition to measuring brushing, the toothbrush can also include sensors which detect other measurable information including: a temperature sensor, pH level sensor and/or camera(s). A temperature sensor can inform the user of a fever. In an embodiment, the system can record the normal temperature of the user and based upon the normal temperature or normal temperature cycle inform (Basal body temperature can vary based upon hormonal cycle) the user if he or she has a fever when the measured temperature is two or more degrees greater than normal. Because the system has a recorded history of the user's normal body temperature, the fever notification provided by the system can be much more accurate than a normal thermometer reading.

The pH level sensor can provide a record of the user's pH level within the mouth. A normal neutral pH level of about 7 is important for the growth of healthy bacteria. However, a pH level that is more acidic will cause the healthy bacteria to be replaced with unhealthy bacteria that can cause tooth decay. The pH level sensor can determine if the pH level in the mouth is changing and emit a warning signal when the pH level drops below 5.5. The user can respond by reducing the time that the mouth is exposed to acidic fluids and particles such as sodas or sugars to increase the mouth's pH level.

The camera can record the color of the user's teeth over time. This can be useful in detecting changes in the color of the user's teeth. A dark tooth can indicate that the nerves associated with the tooth are damaged and the tooth can be dead. In an embodiment, the system can emit a warning signal to an output device informing the user of any teeth that are discolored. The color sensor can also be used to monitor and record the changes in color when whitening products or treatments are used. Because the color can change very gradually, the system can provide exact color measurements that can help qualify the color change.

BRIEF DESCRIPTION OF THE DRAWINGS

The present application can be best understood by reference to the following description taken in conjunction with the accompanying figures, in which like parts may be referred to by like numerals.

DETAILED DESCRIPTION

Figure 1:
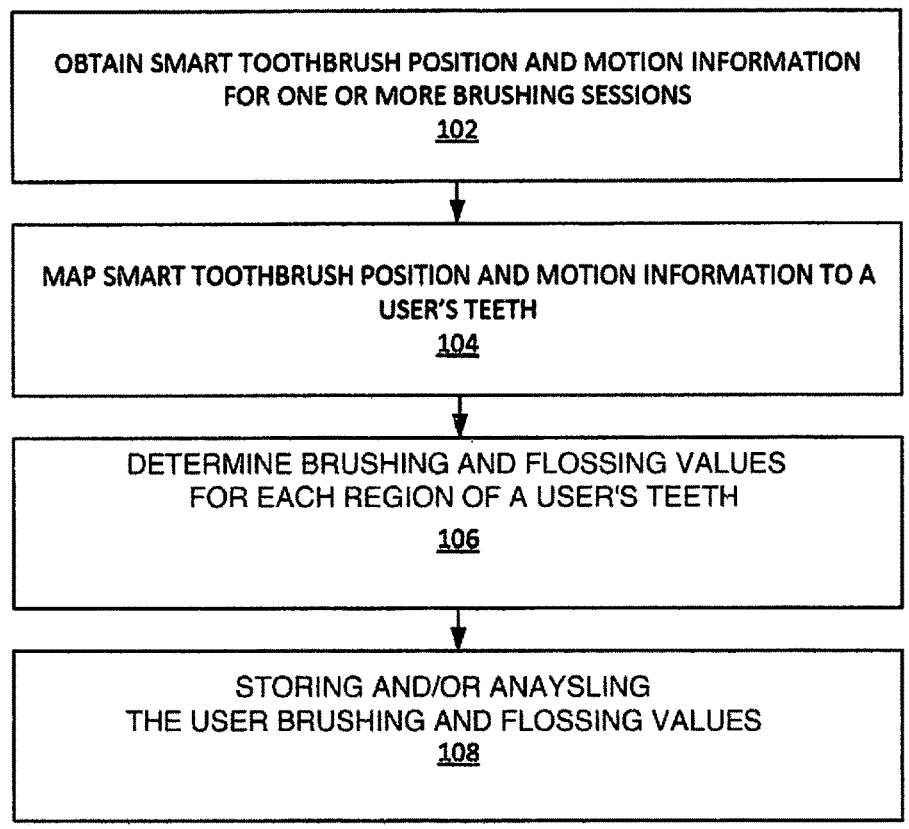
FIG. 1 depicts an example process for implementing a smart toothbrush, according to some embodiments.

Disclosed are a system, method, and article of manufacture of a smart toothbrush that can include a flossing attachment. The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments.

Reference throughout this specification to "one embodiment," "an embodiment," "one example," or similar language means that a particular feature, structure, or characteristic described in connection with the embodiment is included in at least one embodiment of the present invention. Thus, appearances of the phrases "in one embodiment," "in an embodiment." and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connector may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Process Overview

FIG. 1 depicts an example process 100 for implementing a smart toothbrush or tooth cleaning device, according to some embodiments in step 102 of process 100 smart toothbrush position and motion information is obtained for one or more teeth brushing sessions. A smart toothbrush can be an electric toothbrush that has a vibrating head and includes various sensors (e.g. position and motion sensors), computer processors, data storage capabilities and/or networking capabilities. As used herein, an electronic toothbrush can be powered by an electric power supply usually by a battery to move the brush head rapidly, either oscillating side to side, or rotation-oscillation (where brush heads rotate in one direction and then the other) and the like. Position and motion sensors can include such sensors as an accelerometer, a gyroscope, a magnetometer, a compass sensor, and the like. Position and motion sensors can provide position and motion data to one or more processors to a computing system in the smart toothbrush or in communication with the smart toothbrush. In some embodiments, the smart toothbrush can also include pressure sensors that can detect when the head of the smart toothbrush is pressed against an object such as a tooth, as well as, determine the pressure of the brushing bristles on teeth or the pressure of the bristles against the contact area of the teeth. Sensor information can transmitted continuously during brushing and the sensor data can be recorded and time stamped. In the event that the smart toothbrush is communicatively coupled with a computer network (e.g. the Internet, a local wireless network like Bluetooth®, a computer bus like a USB system, a Wi-Fi network, etc.), the position and motion information can be communicated to another computer system (e.g. a server, an application in a smartphone, and the like).

In some embodiments, the smart toothbrush head can include other types of sensors such as lasers, chemical sensors and/or digital cameras that provide additional information about the object in contact with the head portion of the smart toothbrush. In some examples, this information can also be utilized in pathogenic diagnostic processes (e.g. provided to a dentist, utilized by a dental health functionalities that detects dental caries (e.g. tooth cavities), dental diseases and/or pathogens, other oral pathologies, gum receding states, and the like. For example, laser sensors in the smart toothbrush can be utilized to generate a three dimensional topology of the user's teeth and other oral structures.

In step 104, the smart toothbrush position and motion information can be mapped to a user's teeth. The system can store a digital representation of each exposed surface area of the user's teeth and the spaces between adjacent teeth. In an embodiment the system can provide coordinates for the exposed surface areas of the teeth. For example, the system can provide surface information in the form of X, Y and Z coordinates in a point cloud digital representation of the surfaces of the teeth. The system can also input user specific information about the user's teeth such as false or missing teeth. The system may identify false or missing teeth in the point cloud digital representation of the surfaces of the teeth.

In step 106, brushing values for each region of a user's teeth can be determined and flossing values for each adjacent set of teeth can be determined. For example, the brushing value can be derived from such information as length of contact between the region and the bristled brush portion of the smart toothbrush, the detected and/or average pressure of the bristled brush portion against the region of the user's teeth. In an embodiment, the regions of the user's teeth can include all exposed surfaces of each individual tooth. For example, the system can determine or predict the surface areas and regions of the inner, outer and top surfaces of lower teeth or bottom surfaces of upper teeth. In some embodiment, the system can be configured to clean the surface areas of the teeth based upon brush time and brush force or pressure. The system can detect other smart toothbrush motions including: pitch, yaw and roll in a three dimensional space. The system can also detect the positions of adjacent teeth for flossing.

In this way, information regarding the efficacy of one or more teeth brushing and flossing sessions can be determined and/or graphically represented. For example, the system can output a graphical map representing the user's mouth and specific regions of the teeth that have not been properly cleaned and specific teeth that have not been properly flossed. In other embodiments various other output forms of graphically representing the teeth brushing for all regions of the teeth surfaces. In step 108, the brushing and flossing values can be stored and/or analyzed (e.g. either in a local computer system and/or in a remote computer system).

Figures 2, 3:
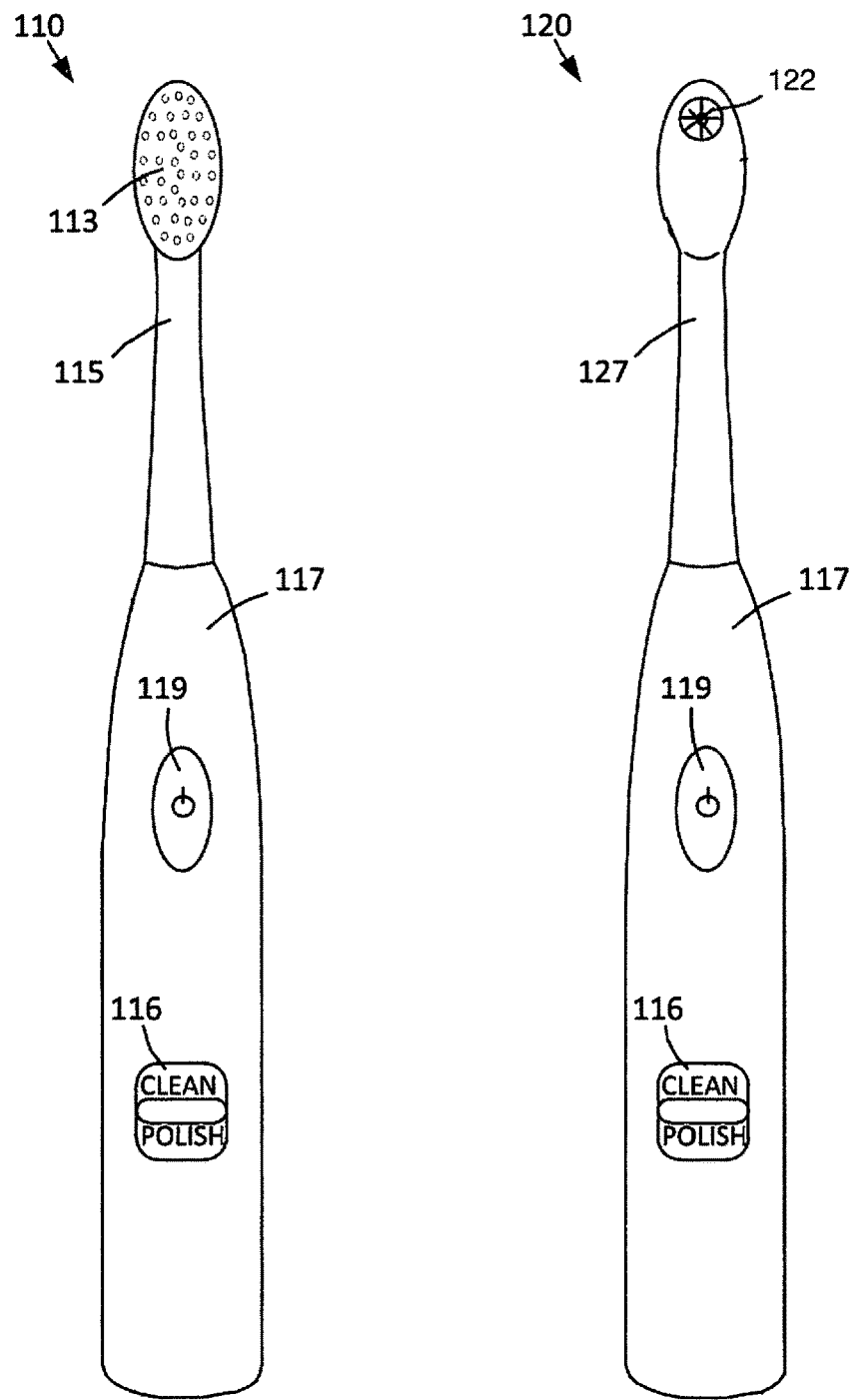
FIG. 2 depicts a front view of a smart toothbrush with bristles
FIG. 3 depicts a front view of a smart toothbrush with sensors.

FIG. 2 depicts an exterior view of an embodiment of a smart toothbrush 110. The smart toothbrush 10 can be an interdental toothbrush, an end-tufted toothbrush, and/or other type of toothbrush. In an embodiment, the toothbrush 110 can have a bristle portion 115 and a handle portion 117. Various user input mechanisms such as an on/off button 119, a speed controller 116, and other controls can be placed on the exterior body of the smart toothbrush 110. The on/off button 119 can turn the brush on or off. The user to control the rate of vibration of the bristles can adjust the speed controller 116. A faster vibration rate can be used to clean the teeth while a slower vibration rate can be used to polish the teeth.

In an embodiment, the bristle portion 115 can be removed from the handle portion 117 as shown in FIG. 2 and replaced with a flossing device as shown in FIG. 3. The flossing device 122 can be a flossing pick construction with an elongated center member with bristles extending outward in a radial pattern. The flossing device 121 will be described in more detail with reference to FIGS. 11-17 below.

Figure 4:
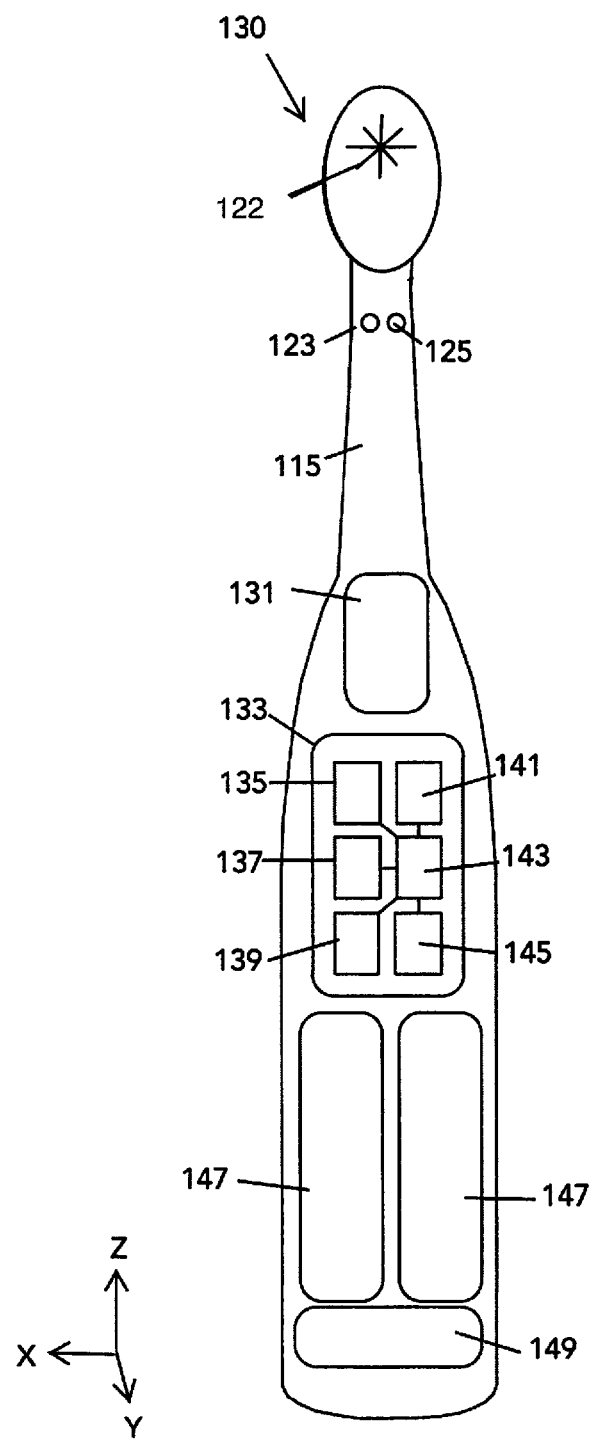
FIG. 4 depicts a front view of a smart toothbrush with internal components, bristles and sensors.

With reference to FIG. 4, in other embodiments, the flossing device 122, pH sensor 123 and/or the camera 125 can be integrated into the bristle portion 115 of the toothbrush 130 so that the bristles can be use to brush the teeth and then the head can be rotated 180 degrees and the flossing unit 122 can be used to floss the teeth. FIG. 4 also illustrates an internal view of the handle portion 117 which can include several system components. The exemplary smart toothbrush 130 can include a power source such as rechargeable batteries 147. In an embodiment inductive power transfer through an induction coil 149 can recharge the rechargeable batteries 147. When the toothbrush 130 is placed in a charger base, a primary coil in the charger base can emit an electromagnetic field, which can transmit power to the induction coil 149. This physical configuration can link the charger coil and the induction coil 149 by electromagnetic induction. Energy flows from the primary coil in the charger to the induction coil 149 in the toothbrush 149. The two ends of the induction coil 149 in the toothbrush can be coupled to the positive and negative electrodes to recharge the rechargeable battery or batteries 147.

The batteries 147 can power various sensors as well as computing systems for sensor driver functionalities, sensor data management and/or sensor data communication. In an embodiment, the toothbrush 130 can include a processor 143 that is coupled to accelerometer 135, gyroscope 137, compass 139 and pressure sensor 145 which can all be mounted on a printed circuit board 133. In an embodiment, the X, Y, Z accelerometer 135, gyroscope 137 and compass 139 can be used to detect the position of the bristles 113 against the user's teeth. The processor 143 can also be coupled to a transmitter or transceiver 145 which can transmit data from the toothbrush 130.

In this example, the Z axis can be aligned with the length of the toothbrush 130 and the bristles can be aligned with the Y axis and the X axis can be perpendicular to the length of the toothbrush 130 and the bristles 113. In other embodiments, the position of the toothbrush 130 can be defined by any other three dimensional coordinate system. Before the toothbrush 130 is used, it can be stored in a vertical position on a charger. This vertical position can be detected by the accelerometer 135 which can detect the vertical acceleration force of gravity. In the stored position, the system can be in a rest mode where sensor data is not being recorded.

When the user picks up the toothbrush 130 and the bristles 113 can be placed against the teeth. The system can detect pressure of the bristles 113 against the teeth with the pressure sensor 145 and/or a horizontal position of the toothbrush 130 with the accelerometer 135 and the actuation of the on/off button. In an embodiment, the system may require one or more of: pressure signal, horizontal position signal and on button actuation to begin transmitting and/or recording position signals.

During the recording process, the system can record the accelerometer, gyroscope and compass signals and based upon these signals the system can determine the position of the bristles 113 against the teeth. For example, when the top surfaces of the lower teeth are brushed, the bristles 113 can be positioned facing down and the accelerometer can detect a positive Y direction acceleration. Conversely, when the bottom surfaces of the upper teeth are brushed, the bristles 113 can be positioned facing up and the accelerometer can detect a negative Y direction acceleration.

TABLE 1

| Teeth Surfaces | X Accel | Y Accel |
| --- | --- | --- |
| Top of front bottom teeth | 0 | −Gravity |
| Top of right molars bottom teeth | 0 | −Gravity |
| Top of left molars bottom teeth | 0 | −Gravity |
| Bottom of front top teeth | 0 | +Gravity |
| Bottom of right molars top teeth | 0 | +Gravity |
| Bottom of left molars top teeth | 0 | +Gravity |
| Outer front teeth | + or −Gravity | 0 |
| Outer right molars | +Gravity | 0 |
| Outer left molars | −Gravity | 0 |
| Inner front teeth | + or −Gravity | 0 |
| Inner right molars | −Gravity | 0 |
| Inner left molars | +Gravity | 0 |

The compass 139 and/or gyroscope 137 can detect the horizontal rotation (yaw) of the toothbrush 130. With the bristles up or down the rotation will be about the y axis and if the bristles and floss device are in horizontal positions for cleaning the inner or outer surfaces the rotation can be about the x axis. The horizontal rotation or yaw position of the toothbrush can be measured and the system may detect a rotational difference of up to 90 degrees as the user brushes moves the bristles from the front teeth to the molars or from the molars to the front teeth. The horizontal rotation or yaw position of the toothbrush can be measured and the system may detect a rotational difference of up to 90 degrees as the user flosses with the floss device. The output signals from the compass sensors 137 and/or gyroscope sensors 139 can be used to identify the position of the bristles and floss device as shown in Table 2 below. The accelerometer signals can indicate the orientation of the bristles and floss device and the rotational sensors can detect the angular position of the toothbrush bristles and floss device. Each angular position can correspond to a specific tooth and floss area between adjacent teeth. For example, the alignment of the toothbrush with the front teeth will be almost 90 degrees offset in rotational position relative to toothbrush against the molars. After this information is recorded, the system can review the data and determine if sufficient brushing time and brushing force has been applied to each tooth. Because this analysis can be very fast, the system can immediately inform the user if a tooth or a region of the mouth has not been properly brushed.

TABLE 2

| Brushing Area<br>Brushing Movement | X<br>Accel | Y<br>Accel | X<br>Rotation | Y<br>Rotation |
|---|---|---|---|---|
| Tops of right lower teeth<br>Front teeth to molars | 0 | −Grav | 0 | CCW<br>Rotation |
| Tops of left lower teeth<br>Front teeth to molars | 0 | −Grav | 0 | CW<br>Rotation |
| Bottoms of right upper teeth<br>Front teeth to molars | 0 | +Grav | 0 | CW<br>Rotation |
| Bottoms of left upper teeth<br>Front teeth to molars | 0 | +Grav | 0 | CCW<br>Rotation |
| Outer right surfaces<br>Front teeth to molars | +Grav | 0 | CW<br>Rotation | 0 |
| Outer left surfaces<br>Front teeth to molars | −Grav | 0 | CW<br>Rotation | 0 |
| Inner right surfaces<br>Front teeth to molars | −Grav | 0 | CCW<br>Rotation | 0 |
| Inner left surfaces<br>Front teeth to molars | +Grav | 0 | CCW<br>Rotation | 0 |

In Table 2 the descriptions of movements are from the front teeth to the molars. However, in other embodiments, the system can be configured to detect the movement of the toothbrush and flossing device from the molars to the front teeth. Because the sensor detections can be the same for the outer and inner surfaces of the upper and lower sets of teeth, the system may require a specific sequence of brushing. For example, the system may require the user to brush or floss the lower set of teeth before brushing the upper set of teeth or visa versa. The system may distinguish the brushing and flossing of the upper and lower sets of teeth based upon the cleaning of the upper surfaces of the lower teeth or the lower surfaces of the upper teeth. More specifically, if the sensors detect brushing or flossing of an upper surface this would indicate that the lower set of teeth are being brushed and flossed. If a lower surface brushing or flossing is detected this would indicate that the upper set of teeth are being brushed or flossed. In an embodiment, the user may press a signal button to indicate that the user is transitioning from upper to lower or from lower to upper sets of teeth.

The smart toothbrush 130 can also include various mechanical systems for operating the vibrating brush and flossing portions. For example, the smart toothbrush can include a motor 131. In some embodiments, the motor 131 can be controlled, in part, according to sensor data. For example, the speed of the vibrating brush and flossing portions can be modified based on such factors as: sensed pressure values, location and/or orientation of the vibrating brush portion, motions of the smart toothbrush controlled by a user, etc. For example, the speed of the vibrating brush portion can be sped up when it is detected that the brush in a region that the user historically spends less time brushing on average in this way, various aspects of the smart toothbrush can be utilized to compensate for a user's inadequate brushing pattern. Additionally, the speed of the vibrating brush and floss portions can be varied for haptic alerts that can transmit various information to a user (e.g. pulsing patterns can notify the user to brush and floss the region of teeth longer, to move to another region of teeth, etc.).

Figure 5:
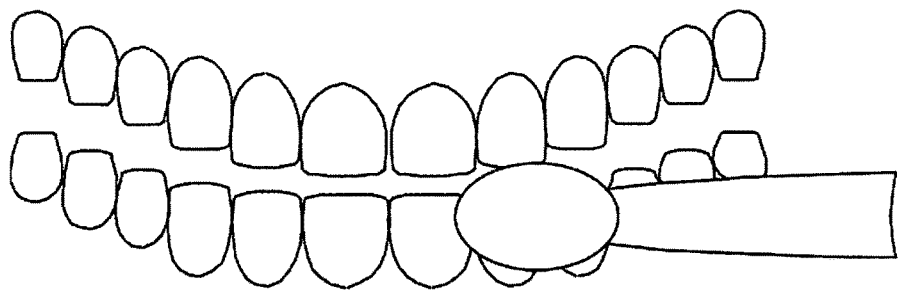
FIGS. 5 and 6 depict an example exterior view of a smart toothbrush cleaning a user's teeth, according to some embodiments.
Figure 6:
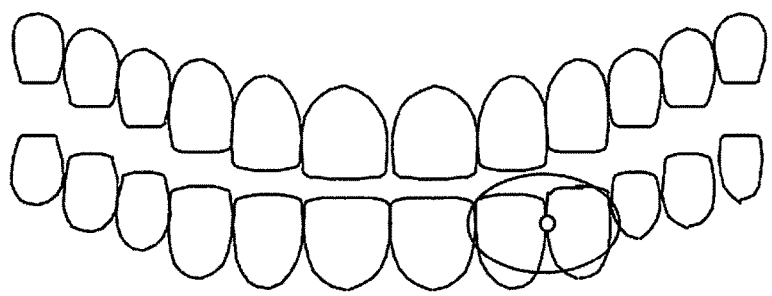

FIG. 5 further depicts an example use of the smart toothbrush. A mouth level view of the portion of the teeth being brushed can be generated in substantially real time. The application can operate in another user computing device (e.g. a tablet computer, a smart phone, smart glasses, etc.) that receives data from the smart toothbrush and flossing device. FIG. 6 illustrates the flossing device of the toothbrush between two adjacent lower teeth.

Figure 7:
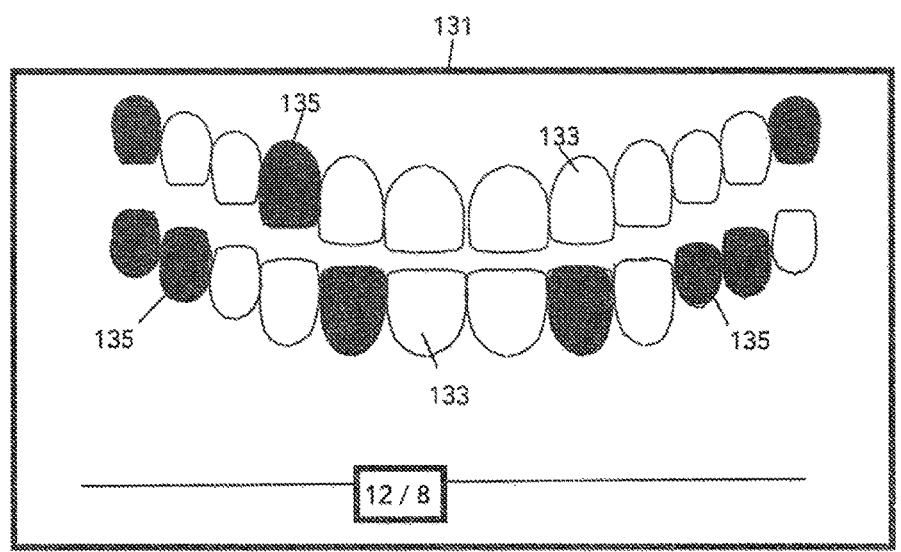
FIG. 7 depicts an example screenshot provided with a smart toothbrush application operative in a computing device, according to some embodiments.

FIG. 7 depicts an example screenshot provided with a smart toothbrush application operative in a computing device, according to some embodiments. The user's toothbrushing and flossing information can be obtained from a smart toothbrush and the tooth-brushing and flossing information can be logged and stored. A smart toothbrush application can retrieve the tooth-brushing session information for analysis. For example, the smart toothbrush application can determine which of the user's teeth are more prone to the development of plaque (e.g. based on aggregated user toothbrushing session information). The smart toothbrush application can determine which areas of the user's teeth may benefit from additional brushing time (e.g. thirty more seconds of brushing each session, fifteen seconds of brush each session, etc.) and flossing. The smart toothbrush application can render this information for display as shown in FIG. 7. In this example, the display 131 can include a graphical representation of the user's teeth with normal white teeth 133 and colored teeth 135. The colored teeth 135 can provide a color coded indication of problem areas. For example, the colored teeth 135 may indicate that the tooth is plaque prone and the user will need to spend more time brushing and flossing these teeth. The color of the colored teeth 135 may indicate the additional brushing and flossing time needed. For example, a red colored tooth 135 may require 30 extra seconds while a yellow colored tooth 135 may require 15 extra seconds of brushing or flossing. The display 131 can include various display and/or user preference options. For example, the display of FIG. 7 can include a slider that enables the user to brushing and flossing behavior as a function of time. In this example, the slider is at 12/8 which can indicate a specific date of the recorded data. Because the teeth measurements are recorded an extended history of the teeth can be recorded. In this way, a user can monitor any improvements in her tooth brushing and flossing regime.

Exemplary Environment and Architecture

Figure 8:
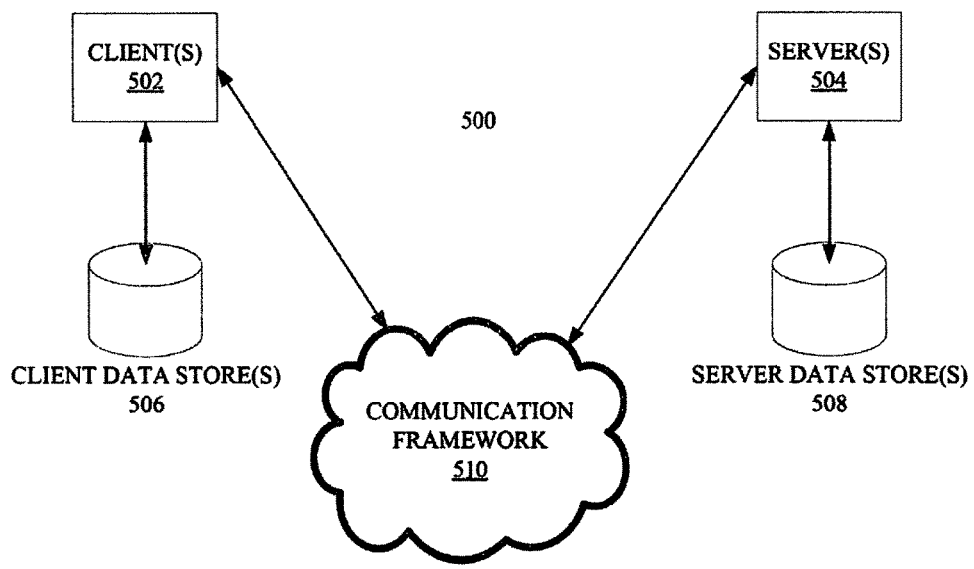
FIG. 8 is a block diagram of a sample computing environment that can be utilized to implement some embodiments.

FIG. 8 is a block diagram of a sample computing environment 500 that can be utilized to implement some embodiments. The system 500 further illustrates a system that includes one or more client(s) 502. The client(s) 502 can be hardware and/or software (e.g., threads, processes, computing devices). The system 500 also includes one or more server(s) 504. The server(s) 504 can also be hardware and/or software (e.g., threads, processes, computing devices. One possible communication between a client 502 and a server 504 may be in the form of a data packet adapted to be transmitted between two or more computer processes. The system 500 includes a communication framework 510 that can be employed to facilitate communications between the client(s) 502 and the server(s) 504. The client(s) 502 are connected to one or more client data store(s) 506 that can be employed to store information local to the client(s) 502. Similarly, the server(s) 504 are connected to one or more server data store(s) 508 that can be employed to store information local to the server(s) 504.

In some embodiments, system 500 can be include and/or be utilized by the various systems and/or methods described herein to implement process 100. For example, the specified content of step 102 can be stored in 506 and/or 508. User login verification can be performed by server 504. Client 502 can be in an application (such as a web browser, augmented reality application, text messaging application, email application, instant messaging application, etc.) operating on a computer such as a personal computer, laptop computer, mobile device (e.g. a smart phone) and/or a tablet computer. In some embodiments, computing environment 500 can be implemented with the server(s) 504 and/or data store(s) 508 implemented in a cloud computing environment.

Figure 9:
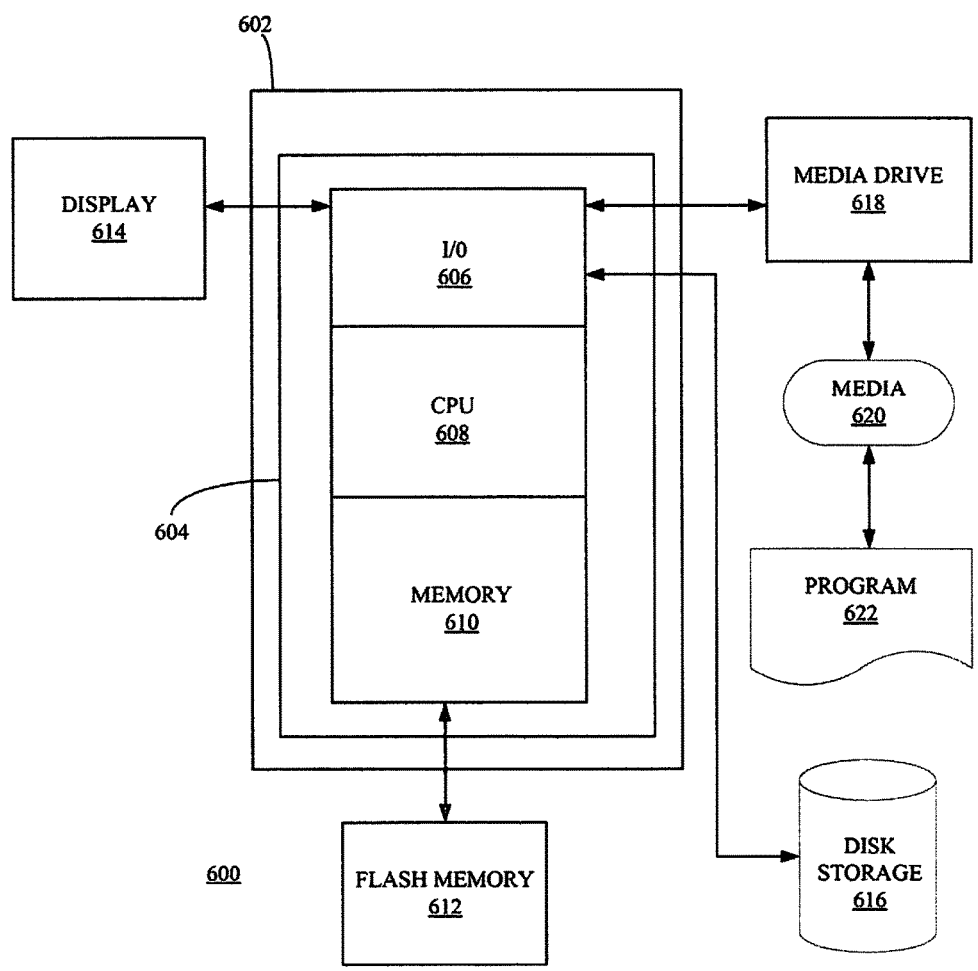
FIG. 9 depicts an exemplary computing system that can be configured to perform any one of the processes provided herein.

FIG. 9 depicts an exemplary computing system 600 that can be configured to perform any one of the processes provided herein. In this context, computing system 600 may include, for example, a processor, memory, storage, and I/O devices (e.g., monitor, keyboard, disk drive, Internet connection, etc.). However, computing system 600 may include circuitry or other specialized hardware for carrying out some or all aspects of the processes. In some operational settings, computing system 600 may be configured as a system that includes one or more units, each of which is configured to carry out some aspects of the processes either in software, hardware, or some combination thereof.

FIG. 9 depicts computing system 600 with a number of components that may be used to perform any of the processes described herein. The main system 602 includes a motherboard 604 having an I/O section 606, one or more central processing units (CPU) 608, and a memory section 610, which may have a flash memory card 612 related to it. The I/O section 606 can be connected to a display 614, a keyboard and/or other user input (not shown), a disk storage unit 616, and a media drive unit 618. The media drive unit 618 can read/write a computer-readable medium 620, which can contain programs 622 and/or data. Computing system 600 can include a web browser. Moreover, it is noted that computing system 600 can be configured to include additional systems in order to fulfill various functionalities. In another example, computing system 600 can be configured as a mobile device and include such systems as may be typically included in a mobile device such as GPS systems, gyroscope, accelerometers, cameras, augmented-reality systems, etc.

Figure 10:
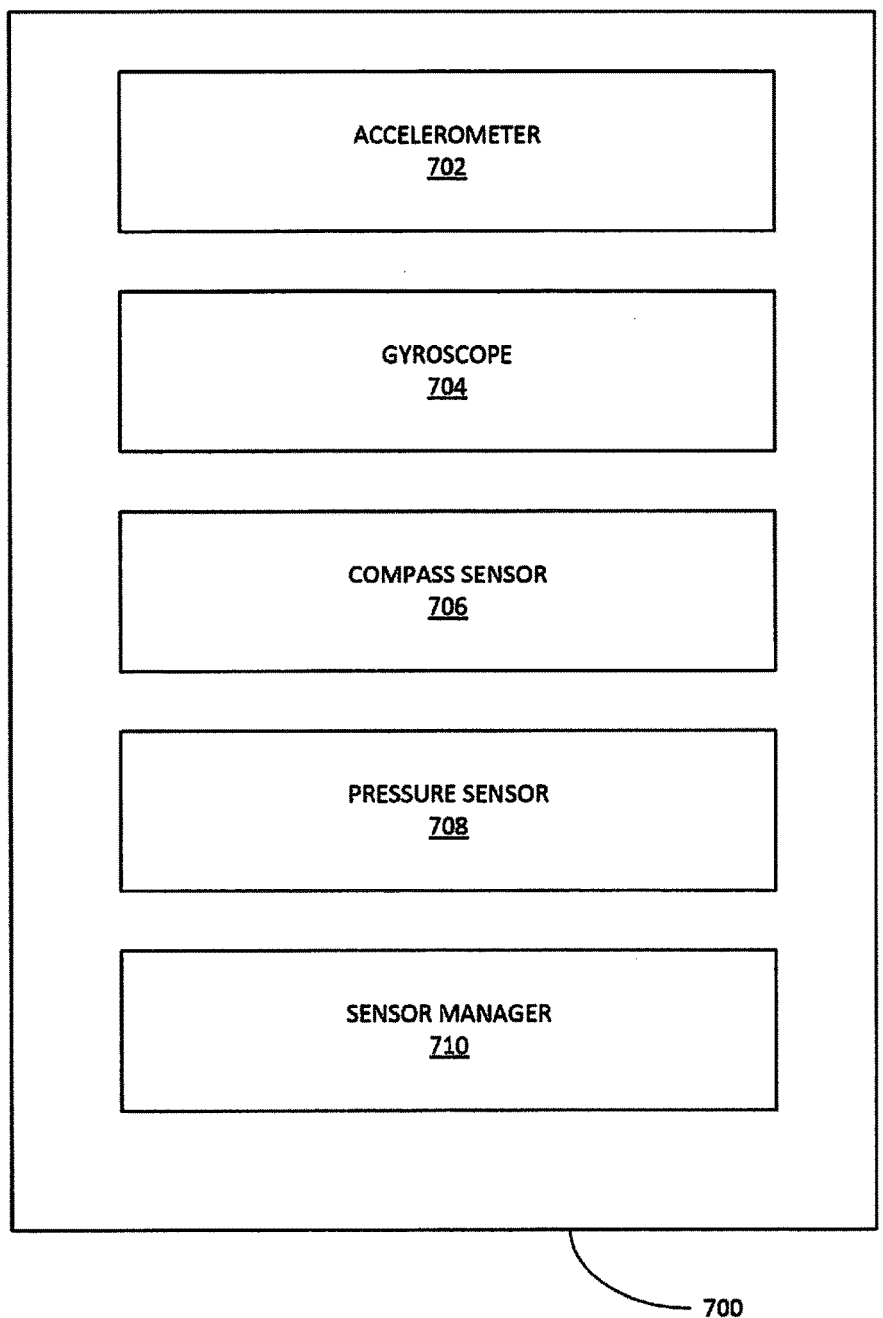
FIG. 10 illustrates an example motion detection and tracking system of a smart toothbrush, according to some embodiments.

FIG. 10 illustrates an example motion detection and tracking system 700 of a smart toothbrush, according to some embodiments. System 700 can include an accelerometer 702. Accelerometer 702 can measure linear (e.g. translational) change in the movement of the smart toothbrush. When an object is moved from one point to another in a straight line, acceleration and deceleration can be measured. In some example, a free fall acceleration due to gravity equals 1.0 g, and forms the basic unit of measurement. Single- and multi-axis accelerometers can be detected. The magnitude and direction of the acceleration as a vector quantity, and can be used to sense orientation, vibration and shock. As used herein, angular velocity, also referred to as angular acceleration, can be the rate of change of angular displacement with respect to time. Gyroscope(s) 704 can measure angular velocity in units of degrees per second. Gyroscope(s) 704 can also measure the angular rate by measuring the Coriolis force generated when an internal vibrating mass is rotated. As used herein, the Coriolis force can be the force causing deflection of moving objects when they are viewed from a rotating reference frame. This causes a translational force in the other orthogonal direction. Gyroscope(s) 704 can also measure the rate of rotation of the smart toothbrush. Compass sensor 706 can detects the earth's magnetic field and functions as a compass. Pressure sensor(s) 708 can measure various pressures exerted on and/or by the smart toothbrush. Pressure measurement can be an indirect measure, and is optional in some embodiments. Pressure sensor(s) 708 can sense the force exerted by the brushing system, measuring the electrical current used by it. At first is assumed a linear relationship between current and force.

Information from these sensors can be converted into electrical signals and processed by sensor manager 710. Sensor manager 710 can aggregate sensor data and determine a position and motion of the smart toothbrush as a function of time. Sensor manager 710 can include various sensor drivers for controlling sensor operations. Sensor manager 71 can include an embedded hardware accelerator, such as a Digital Motion Processor™ (DMP). A DMP can be provide sensor fusion by combining the outputs from the multiple motion sensors. For example, a DMP can track the sensor outputs of the following sensors: a 3-Axis Accelerometer 702, a 3-Axis Gyroscope 704, a 3-Axis Magnetometer (e.g. compass sensor 706), a Thermometer, and/or a pressure sensor 708. The DMP firmware can combine calibrated accelerometer, gyroscope, pressure measurement, temperature and compass sensor outputs into a single data stream for Smartphone software to easily incorporate motion tracking. As a result of integrating multiple sensors onto the same die and package and providing a DMP, Sensor manager 710 can bypass traditional calibration steps used with discrete sensor solutions. In one example, sensor manager 710 can measure movement at 200 Hz and obtain new data each 5 ms. In one example, this granularity in the tracking process can enable the sensor manager 710 to recover (e.g. using Nyquist theorem) changes in the measured values at 10 ms (e.g. 100 Hz) intervals. In some embodiments, an Invensense MPU-9150 motion tracker can be utilized in the smart toothbrush.

In some embodiments, the user places the smart toothbrush in a known position, for example the frontal teeth. Then, it begins the brushing process. Smart toothbrush can collects data and transmits them to the Smartphone in "online" mode, or stores it in offline mode. The transmitted data are the "fused" data, including the information of all the sensors. Smart toothbrush can track brushing times and sessions. This information can be provided to a smartphone application. The smartphone application can process the data and provide the user feedback about the quality of the brushing. The smartphone application can store the information. In some examples, this information can also be provided to medical professionals (e.g. the user's dentist).

In an embodiment, the cleaning by brushing is based upon force within a predetermined force range and time within a predetermined time range against all outer surfaces of the teeth. If the force or time of the bristles movement against any area of the teeth does not fall within the predetermined force and time requirements, the processor can transmit an error signal to an output device to inform the user that there was an error in the teeth cleaning. For example, if the predetermined force of the bristles against the teeth is between about 0.25 to 0.5 LB force, the system can emit a signal to the output device if the force actually being applied is too strong or too light which is outside the predetermined force range. In an embodiment, the system can also emit a signal indicating that the force correction has been made and the adjusted force is within the predetermined force range. In an embodiment, if the force is not within the required range, the system can emit a signal to an output device to inform the user to increase or decrease the force applied to the brush.

Alternatively, the force can be measured as a pressure based upon the surface area of the bristles of the toothbrush. For example, a bristle portion may have an area of about 0.5 square inches and the predetermined pressure for proper brushing can be between about 0.12 to 0.25 PSI. If the detected pressure is outside of this predetermined range, the system can emit a signal to an output device to inform the user to correct the applied pressure by increasing or decreasing the applied force.

Similarly, the system can inform the user if the time spent over any area of the teeth is too long or too short. The system can compare the position of the bristles with a digital representation of the user's mouth and determine how much time is spent over each surface area. The system can inform the user if too little brushing time has been spent on any area. However, because the molars have more surface area than the front teeth, the system can require that more brushing time be applied to the molars than the front teeth. For example, in an embodiment, the total time spent brushing may be 120 to 150 seconds. A total of 60 to 75 seconds of brushing time can be applied to the upper teeth and 60 seconds applied to the lower teeth. Of the 60 to 75 seconds applied to the upper and lower teeth, 2×40 to 50 seconds may be applied to the molars and 2×20 to 25 seconds may be applied to the front teeth.

In an embodiment, the flossing is based upon position and time within a predetermined time range between adjacent teeth. If the position or time of the flossing device between the teeth does not fall within the predetermined time requirements, the processor can transmit an error signal to an output device to inform the user that there was an error in the teeth cleaning. For example, in an embodiment, the total time spent flossing may be 120 to 150 seconds. A total of 60 to 75 seconds of flossing time can be applied to the upper teeth and 60 seconds applied to the lower teeth. Of the 60 to 75 seconds applied to the upper and lower teeth, 2×40 to 50 seconds may be applied to the molars and 2×20 to 25 seconds may be applied to the front teeth.

In an embodiment, the brushing times can be configurable based upon the specific teeth of the user. For example, many people have crown, implants or have their wisdom teeth removed. In an embodiment, the system can create a digital representation of the surfaces of the teeth based upon the actual live teeth of the user which can be stored in a user database electronic memory. With reference to Table 2 below, the system can input the information about each of the user's teeth. In this example, the user has an implant at the top left quadrant II cuspid. The system may therefore not require as much brushing time be applied to the false or missing teeth when determining the proper brushing times and forces.

TABLE 2

|  | Top Right Quadrant I | Top Left Quadrant II | Bottom Right Quadrant III | Bottom Left Quadrant IV |
| --- | --- | --- | --- | --- |
| Central Incisor | X | X | X | X |
| Lateral Incisor | X | X | X | X |
| Cuspid | X | Implant | X | X |
| 1st Bicuspid | X | X | X | X |
| 2nd Bicuspid | X | X | X | X |
| 2nd Bicuspid | X | X | X | X |
| 1st Molar | X | X | X | X |
| 2nd Molar | X | X | Crown | Crown |
| 3rd Molar | Removed | X | Removed | Removed |

For each tooth, the system can provide surface area and brushing/flossing location information based upon an estimated surface area for each tooth. The brushing surface areas for each tooth can include inner surfaces, top surfaces and outer surfaces. The flossing surface areas for each tooth can include adjacent surfaces of teeth. These surface areas can vary depending upon the types tooth. For example, a top surface of a central incisor will be much smaller than a top surface of a 2nd molar. In an embodiment, the inventive system can have a specified of brushing time associated with each tooth surface as shown in Table 3 below. In Table 3, the numeric values can represent the minimum brushing times in seconds. The brush times for the user's teeth can be stored in a user database electronic memory. In other embodiments, the time applied can be based upon the measured surface areas of the user's teeth and a user with a larger mouth and teeth may require more brushing time than a user with a smaller mouth and teeth.

TABLE 3

|  | Inner Surface | Top Surface | Outer Surface |
| --- | --- | --- | --- |
| Central Incisor | 1 | 0.3 | 1 |
| Lateral Incisor | 1 | 0.3 | 1 |
| Cuspid | 1 | 0.3 | 1 |
| 1st Bicuspid | 1.1 | 0.4 | 1.1 |
| 2nd Bicuspid | 1.2 | 1.2 | 1.2 |
| 1st Molar | 1.5 | 1.5 | 1.5 |
| 2nd Molar | 1.5 | 1.5 | 1.5 |
| 3rd Molar | 1.5 | 1.5 | 1.5 |

In an embodiment, the system can detect the position of the bristles of the toothbrush and the flossing device within the mouth and the force applied to the bristles. The bristles of the toothbrush can be large enough to brush multiple teeth simultaneously. Thus, the detection of brush time by the system can be applied to multiple adjacent teeth. The system can then compare the actual teeth brushing times and forces detected by the system for each surface are of each tooth with a predetermined required brushing time. The system can also compare the actual teeth flossing times detected by the system for surfaces of adjacent teeth with a predetermined required flossing time. The processor can then output a signal to an output device if any one or the tooth or teeth that have not received proper brushing and flossing times. For example, the system can identify the teeth and surfaces that require additional brushing and flossing. In an embodiment, the system can output a signal to a visual display to indicate the teeth and surfaces that need additional brushing and flossing. In another embodiment, the system can provide a position feedback that can track the user's movement of the brush and indicate the teeth surfaces that need brushing and flossing. For example, the system can emit a signal indicating that more brushing or flossing is needed, the system can emit a first audio signal such as a first tone indicating that the brush is not at the proper location. As the user moves the brush close to the proper location, the audio signal can change indicate that the user is getting closer to the missed area of the teeth. When the user has properly positioned the brush, the system can emit a confirmation audio signal such as a confirmation tone and the user can proceed to brush and floss in the missed area of the teeth Because the system can know which teeth are real and false, the system can be configured to only inform the user of missed brushing of real teeth. If the system detects that the user has not brushed or flossed a false tooth, the error signal may not be emitted. However, it can be important for proper gum health to brush at a minimum the bases of the false teeth so in other embodiments, the system will instruct the user to brush the intersection surfaces of the gums for all teeth.

In addition to the position and force sensors, the inventive toothbrush can also include additional sensors for detecting other characteristics of the user's mouth. These additional sensors can include: a temperature sensor for sensing the temperature of a user's mouth, a pH sensor for detecting a pH level of a user's mouth, and/or a camera for detecting a color of a user's teeth. In some embodiments these added sensors can be part of the bristle portion of the toothbrush. However, in other embodiments, the toothbrush can have a modular design with the bristle portion being removable. One or more of the sensors can be mounted on a releasable attachment that can attached to the handle portion of the modular toothbrush when mouth measurements are needed.

In an embodiment the system can collect data from the sensors and emit signals indicating that the measurements are within the proper range or changes in the color of the user's teeth over time. If these sensors indicate that the user's body measurements are not normal, the system can transmit a signal to an output device to warn the user of the abnormal measurement. For example, the system can detect the temperature of a user's mouth. A normal body temperature can be about 98.6 degrees Fahrenheit (F). However, a normal temperature can range from about 97.7 to 99.5 degrees F. A temperature of 99.5 to 101 degrees F. and above can indicate a fever. The system can detect when the user's temperature exceeds the 99.5 and emit a warning when this occurs so the user or guardians of the user will know that the user has a fever and medical attention can be sought.

The pH scale ranges from 1 (most acidic) to 14 (most alkaline) with water having a pH level of 7 (neutral) and the pH level of the mouth can be related to tooth decay based upon the types bacteria that exist within the user's mouth. Many healthy oral microorganisms require a pH around neutrality for growth and are sensitive to extreme changes in acid or alkali. The pH of most surfaces in the mouth is regulated by saliva, which has a normal pH of 6.75-7.25 which is very close to neutral. Optimal pH values for healthy bacterial growth will be provided to the areas of the mouth bathed by saliva.

When exposed to an ambient pH mouth fluids lower than 5.5, the teeth can begin to dissolve or demineralize. This acidic pH levels will also promote the growth of unhealthy bacteria which can replace the healthy bacteria and cause damage to the user's teeth. In an embodiment, the system can issue warnings about the pH level of the user's mouth and detect changes in pH over time. The inventive system can emit a pH warning signal to an output device when a pH of 5.5 or less is detected.

The pH level of the toothpaste being used with the toothbrush and teeth whitening products can influence the readings of the pH sensor. For example, toothpaste can have a pH level between about 8-10. Thus, pH measurements can be raised as a result of the toothpaste. Thus, in an embodiment, the inventive system can use the pH sensor to detect a pH level within the mouth prior to applying toothpaste. The system can then also detect the pH level after toothpaste is applied to detect the altered pH level which should increase the pH level. The system can store this delta pH in memory and use it as an adjustment. For example, if the user's pH level is 6.7 without toothpaste and 7.3 when brushing with toothpaste, the delta pH will be 0.5. If the system detects that the user's pH level is dropping over time, the system can record this information and emit a warning signal to an output device if a pH level of 6.0 or less is detected which can indicate that the pH level without toothpaste is 5.5. The user or guardian of the user can then respond by providing treatments that will increase the pH level to promote the growth of healthy bacteria.

In an embodiment the system can also include a camera which can detect the color(s) of the user's teeth. The normal color of enamel varies from light yellow to grayish (bluish) white. At the edges of teeth where there is no dentin underlying the enamel, the color sometimes has a slightly blue tone. Since enamel is semi translucent, the color of dentin and any material underneath the enamel strongly affects the appearance of a tooth. Thus, the color of teeth can indicate the health of the teeth. In an embodiment, the system can detect the colors of the teeth prior to applying toothpaste and then detect the color during brushing with toothpaste. The system can then identify the altered color based upon a delta color. The system can detect and store the tooth color information in a user database and if a change in a color of a tooth is detected, the system can emit a warning signal to the user. If whitening products are used, the system can record the changes in color so that the user can review the stored color data and quantify the effectiveness of the whitening product.

In an embodiment the teeth cleaning system can have removable and replaceable flossing inserts. The described device can have an electronic mechanism that vibrates the head of the device that is inserted into the mouth of the user as described above. The flossing insert is placed between the adjacent teeth and the teeth cleaning system can vibrate the flossing insert to remove particles between the user's teeth. When the bristles of the flossing insert are worn down, the flossing insert can be removed from the head of the tooth cleaning device and replaced.

Figure 11:
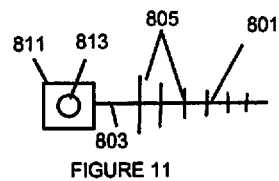
FIG. 11 illustrates a top view of an embodiment of a floss insert.
Figure 12:
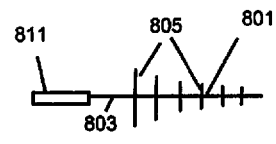
FIG. 12 illustrates a side view of an embodiment of a floss insert.

With reference to FIG. 11 a top view of an embodiment of a flossing insert 801 is illustrated and with reference to FIG. 12, a side view an embodiment of a flossing insert 801 is illustrated. The flossing insert 801 can have a flexible center member 803 with a plurality of bristles 805 that extend outward from the flexible center member 803. The bristles 805 can extend in a perpendicular direction from the flexible center member 803. In the illustrated example, the bristles 805 are shorter towards the distal end of the center member 803 and longer towards the proximal portion of the center member 803. However, in other embodiments, the bristles 805 can be any length or shaped pattern. The flossing inserts 801 can have a mounting insert 811, which is inserted into the head of the tooth-cleaning device. The mounting insert 811 can have rectangular cross section in shape. The mounting insert 811 can also have a center hole 813 which can function as a locking mechanism, which can hold the flossing insert 801 to the head of the tooth-cleaning device.

Figure 13:
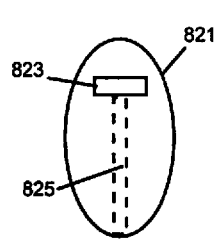
FIG. 13 illustrates a front view of head of a smart tooth cleaning device.
Figure 14:
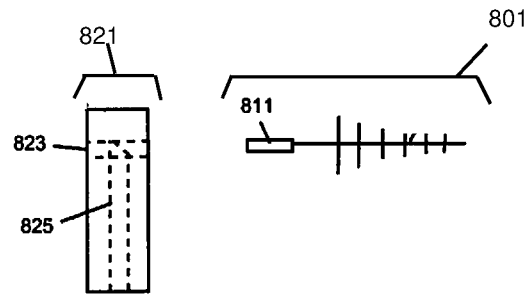
FIG. 14 illustrates a side view of the head of a smart flossing device and the floss insert.

With reference to FIG. 13 a front view of the head 821 of the tooth cleaning device (described above with reference to FIG. 4) and FIG. 14 a side view of the head 821 of the tooth cleaning device and the flossing insert 801 are illustrated. The head 821 can have a slot 823 for the mounting insert 811 of the flossing insert 801. The slot 823 can have a slightly larger rectangular cross section than the mounting insert 811 of the flossing insert 801. The head 821 can have an internal locking bar 825 which is spring loaded which can move into the center hole 813 to lock the mounting insert 811 in the slot 823. The upper end of the internal locking bar 825 can have an angled surface, which can contact the proximal edge of the mounting insert 811 when the flossing insert 801 is inserted into the slot 823. This contact can cause the locking bar 825 to move down and compress a spring when the flossing insert 801 is inserted into the slot 823. When the center hole 813 is positioned in alignment with the locking bar 825, the spring can cause the locking bar 825 to move through the center hole 813 into the slot 823.

Figure 15:
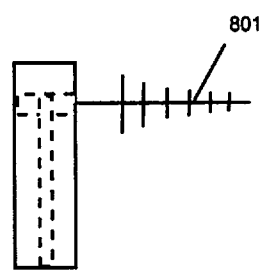
FIGS. 15 and 16 illustrate side views of embodiments of the floss insert inserted into the head of a smart flossing device.

With reference to FIG. 15 a side view of the head 821 of the tooth cleaning device with the flossing insert 801 fully inserted is illustrated. The locking bar 825 is positioned through the center hole 813 of the mounting insert 811 locking the flossing insert 801 to the slot 823 in the head 821 of the tooth cleaning device. The locking bar 825 can be retracted to remove locking bar 825 from the center hole 813 so the flossing insert 801 can be moved from the tooth cleaning device.

Figure 16:
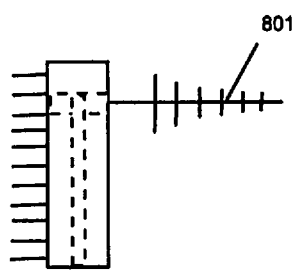
Figure 17:
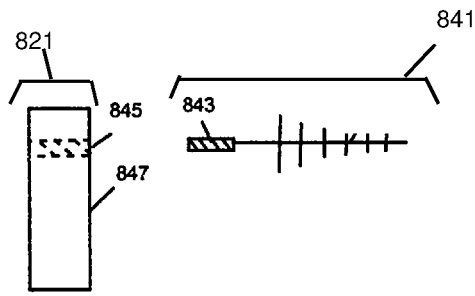
FIG. 17 illustrates a side view of the head of a smart flossing device and the floss insert.

With reference to FIG. 16, a side view of an embodiment of a head 831 is illustrated. In this embodiment, the head 831 includes toothbrush bristles 833 on one side and the flossing insert 801 extending from the opposite side. The user can floss the teeth as described above with the flossing insert 801 and then apply toothpaste to the bristles 833 and brush the teeth with the toothbrush bristles 833 in the manner described above.

While a specific embodiment of the flossing insert 801 has been described, in other embodiments, various other coupling mechanisms can be used to secure the flossing insert to the head of the tooth cleaning device. For example with reference to FIG. 17, the proximal end of the flossing insert 841 can be a threaded rod 843 which can be screwed into a threaded hole in the head 845 of the tooth cleaning device.

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it will be appreciated that the various operations, processes, and methods disclosed herein can be embodied in a machine-readable medium and/or a machine accessible medium compatible with a data processing system (e.g., a computer system), and can be performed in any order (e.g. including using means for achieving the various operations). Accordingly, the specification and drawings are to be regarded in an illustrative rather than a restrictive sense. In some embodiments, the machine-readable medium can be a non-transitory form of machine-readable medium.

What is claimed is:

1. A teeth cleaning system comprising:
    an elongated tooth cleaner comprising:
        a handle portion on a proximal portion of the elongated tooth cleaner;
        a head portion on a distal portion of the elongated tooth cleaner;
        a removable floss pick with a plurality of bristles coupled to the head portion;
        a position sensor for detecting a position of the floss pick relative to a user's teeth;
        a transmitter for transmitting output data from the position sensor; and
        a processor for determining time and movement of the floss pick between the adjacent surfaces of the user's teeth;
        a receiver coupled to the processor for receiving the output data from the position sensor;
        a memory coupled to the processor for storing a digital representation of the user's teeth; and
        an output device coupled to the processor;
    wherein the processor determines if the movement of the floss pick of the elongated tooth cleaner between the adjacent surfaces of the user's teeth is within a predetermined range and the processor transmits a brushing warning signal to the output device when the pressure and the movement of the head portion of the elongated tooth cleaner between the adjacent surfaces of the user's teeth are outside a predetermined range.

2. The teeth cleaning system of claim 1 wherein the head portion of the elongated tooth cleaner further comprises a temperature sensor for detecting a temperature of a user's mouth and the output data transmitted by the transmitter includes temperature data.

3. The teeth cleaning system of claim 2 wherein the processor transmits a temperature warning signal to the output device when the temperature of the user's mouth is outside a predetermined temperature range.

4. The teeth cleaning system of claim 1 wherein the processor determines the time that the head portion of the elongated tooth cleaner is against multiple surfaces of the user's teeth.

5. The teeth cleaning system of claim 1 wherein the toothbrush further comprises a vibration motor for moving the plurality of bristles.

6. The teeth cleaning system of claim 1 wherein the digital representation of the outer surfaces of the user's teeth is a point cloud of data points in a three-dimensional coordinate system.

7. The teeth cleaning system of claim 1 wherein the position sensor includes an accelerometer.

8. The teeth cleaning system of claim 1 wherein the position sensor includes: a gyroscope or a magnetometer.

9. The teeth cleaning system of claim 1 further comprising:
    a movement sensor coupled to the processor.

10. The teeth cleaning system of claim 9 wherein the movement sensor includes: an accelerometer, a gyroscope or a magnetometer.

11. The teeth cleaning system of claim 1 further comprising:
    a pH sensor coupled to the processor mounted in the elongated tooth cleaner wherein
    a pH warning signal is transmitted from the processor to the output device when the pH level of the user's mouth is outside a predetermined pH level range.

12. The teeth cleaning system of claim 11 wherein the pH sensor detects the pH level of the user's mouth before toothpaste is placed on the user's teeth and the pH level of the user's mouth after toothpaste is placed on the user's teeth.

13. The teeth cleaning system of claim 11 wherein the pH warning signal is transmitted from the processor to the output device when the pH level changes over time.

14. The teeth cleaning system of claim 11 wherein the pH warning signal is transmitted from the processor to the output device when the pH level is 5.5 or less.

15. The teeth cleaning system of claim 1 further comprising:
    a camera coupled to the processor mounted in the elongated tooth cleaner for detecting a color of a user's teeth wherein plaque is detected by the color of the user's teeth; and
    a user database coupled to the processor for storing the color of the user's teeth.

16. The teeth cleaning system of claim 1 further comprising:

a force sensor coupled to the processor for detecting a pressure of the bristles against the user's teeth.

17. The teeth cleaning system of claim 1 further comprising:
a user database coupled to the processor for storing the time and the movement of the floss pick.

18. The teeth cleaning system of claim 1 further comprising:
a display coupled to the processor for displaying a graphical representation of the user's teeth wherein the visual display can indicate surfaces that need additional flossing.

19. The teeth cleaning system of claim 1 further comprising:
an audio output coupled to the processor wherein the audio output emits multiple tones wherein a first tone indicates that the elongated tooth cleaner is not at the proper location.

20. The teeth cleaning system of claim 1 further comprising:
a toothbrush coupled to the head portion of the elongated tooth cleaner.

\* \* \* \* \*